United States Patent [19]

Brittain et al.

[11] Patent Number: 5,633,497

[45] Date of Patent: May 27, 1997

[54] SURFACE COATING TO IMPROVE PERFORMANCE OF ION TRAP MASS SPECTROMETERS

[75] Inventors: Robert D. Brittain; Mingda Wang, both of Walnut Creek, Calif.

[73] Assignee: Varian Associates, Inc., Palo Alto, Calif.

[21] Appl. No.: 552,417

[22] Filed: Nov. 3, 1995

[51] Int. Cl.[6] .................................................. H01J 49/42
[52] U.S. Cl. ............................................ 250/292; 250/291
[58] Field of Search ................................. 250/292, 290, 250/291

[56] References Cited

U.S. PATENT DOCUMENTS

| 4,126,781 | 11/1978 | Siegel | 250/396 R |
| 4,704,532 | 11/1987 | Hua | 250/292 |
| 5,021,654 | 6/1991 | Campbell et al. | 250/287 |
| 5,055,678 | 10/1991 | Taylor et al. | 250/292 |

*Primary Examiner*—Jack I. Berman
*Attorney, Agent, or Firm*—Edward Berkowitz

[57] ABSTRACT

The interior surfaces of an ion trap or ionization chamber is coated with an inert, inorganic non-metallic insulator or semiconductor material for the passivation of such surfaces so as to minimize absorption, degradation or decomposition of a sample in contact with the surface.

9 Claims, 3 Drawing Sheets

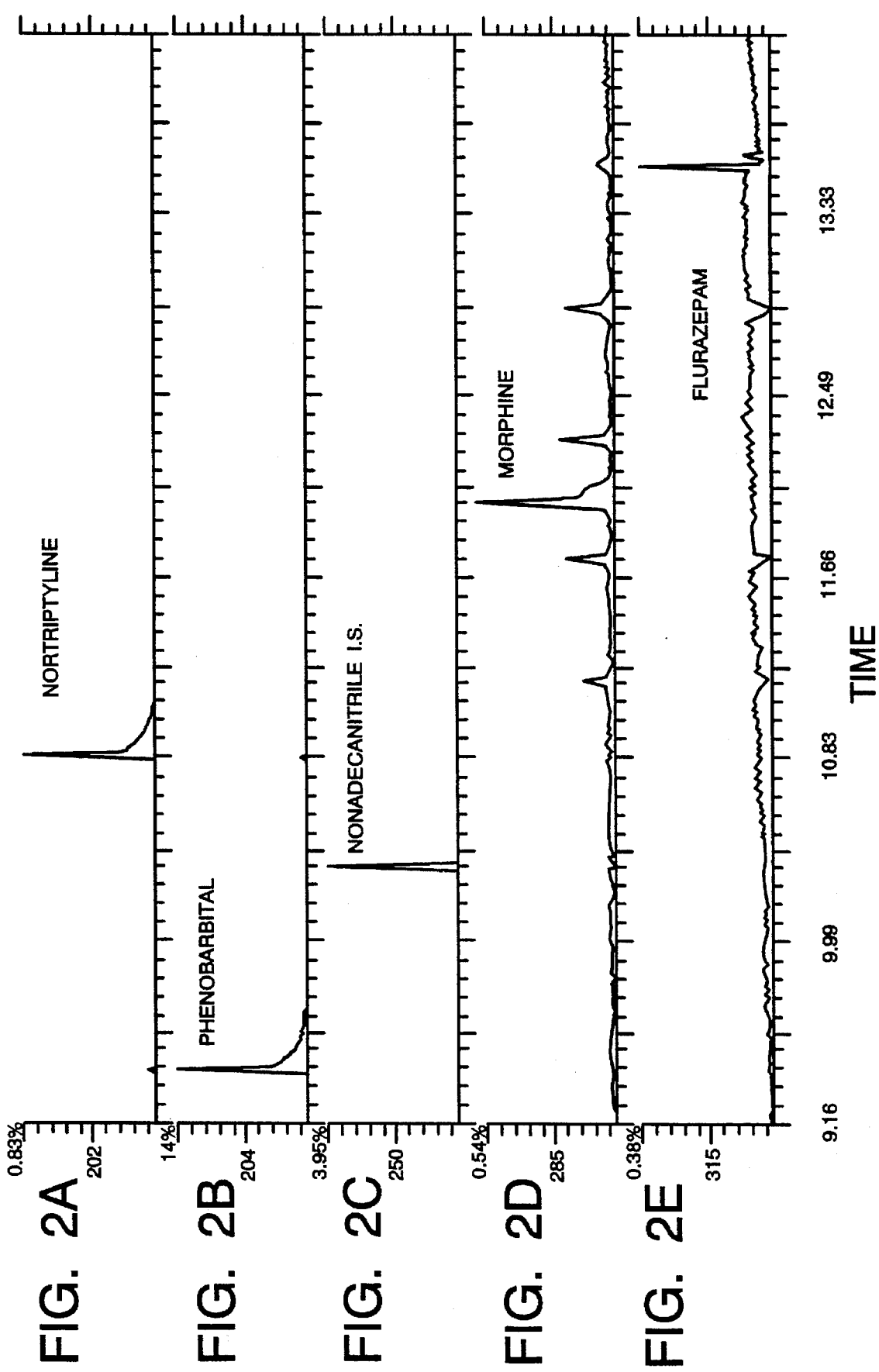

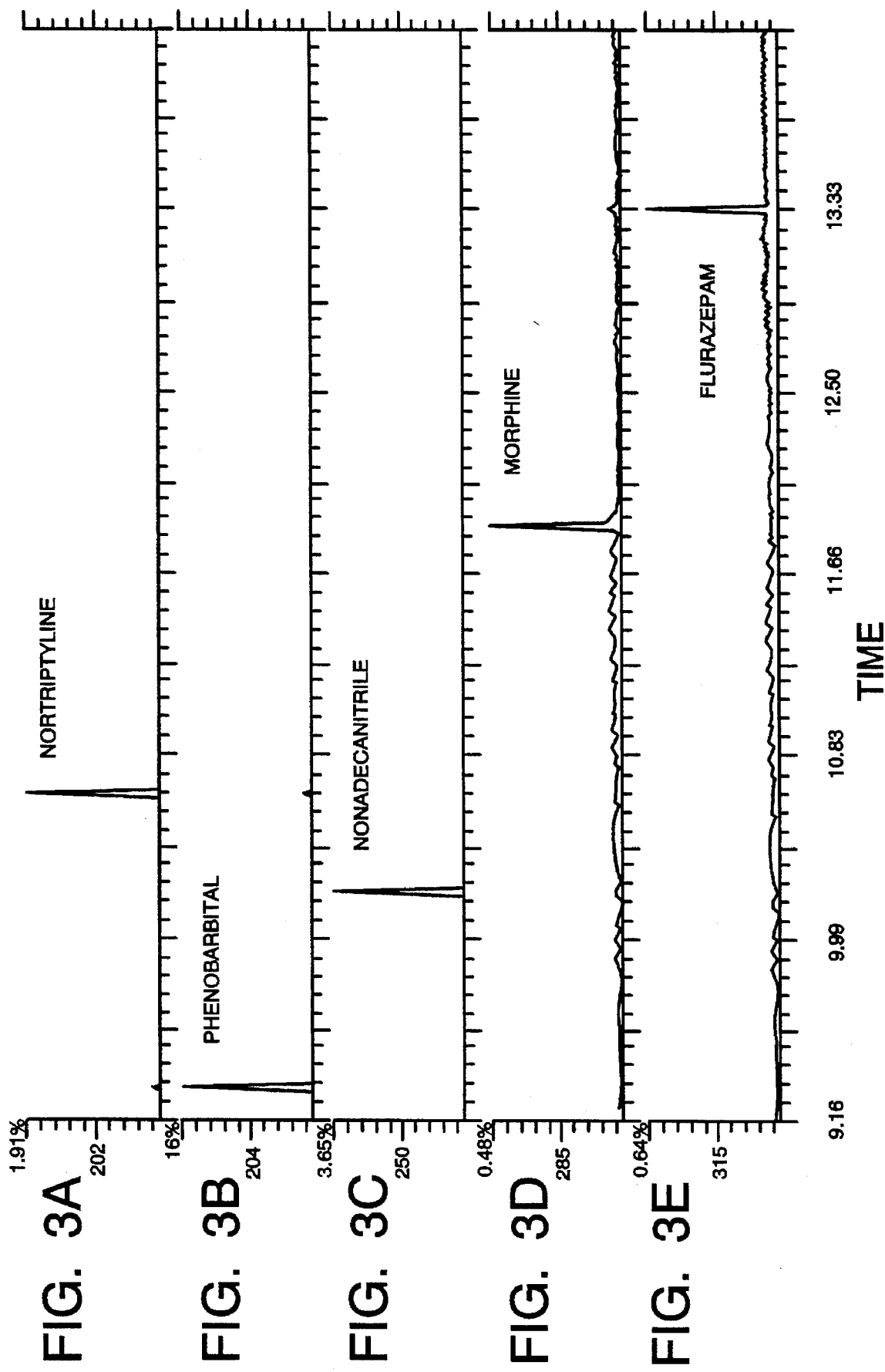

SURFACE COATING TO IMPROVE PERFORMANCE OF ION TRAP MASS SPECTROMETERS

FIELD OF THE INVENTION

This invention relates to apparatus for analysis of samples and especially to equipment wherein interior surfaces of such apparatus are in contact with a sample as more particularly occurs in ionization chamber and ion trap apparatus.

BACKGROUND OF THE INVENTION

In apparatus for chemical analysis of a sample, the sample, in some form is frequently exposed to surfaces such as electrodes for establishing desired electric field, within the interior of a detector. The interaction of sample substance on these surfaces may create an undesired effect. These surfaces, for example, may catalyze some chemical reaction by which the chemical analysis is distorted, or these surfaces may be at an elevated temperature which promotes decomposition of sample molecules in contact therewith.

Surface-sample molecular interactions may also distort the subsequent analysis of the sample, for example by distortion of the peak shape in a chromatogram due to surface forces acting on the sample at the electrode surfaces which affect retention time within an ion trap or similar detector.

These phenomena are known in the prior art and it was known to reduce the catalytic decomposition effect by applying a specific passivating agent. U.S. Pat. No. 5,055,678 describes the use of chromium or oxidized chromium surfaces for ion trap and ionization chambers. The same reference also describes the use of organic silanizing reagents which chemically bond to specific chemical sites on the electrode surface.

It is desired to achieve a greater degree of isolation between samples and the instrumental environment for an analytical component. The present invention, a fused silica coating (as a specific embodiment) having thickness of the order of 0.02 to 0.1 micron, has been found to substantially improve peak shapes in chromatographic apparatus in comparison with chromium coated stainless steel electrodes of prior art. Fused silica has been shown to have the advantage of not only reducing chemical decomposition at the surface, but also reducing peak tailing due to physical or chemical absorption on the ion trap surfaces.

BRIEF DESCRIPTION OF THE DRAWINGS

FIGS. 2A–E inclusive show mass analyzed chromatograms for five respective samples using a standard ion trap having chromium coated electrodes.

FIGS. 3 A–E show the chromatograms of the samples of FIG. 1A–E, respectively, using the fused the silica coating of the present invention.

DETAILED DESCRIPTION OF THE INVENTION

Figure 1A:
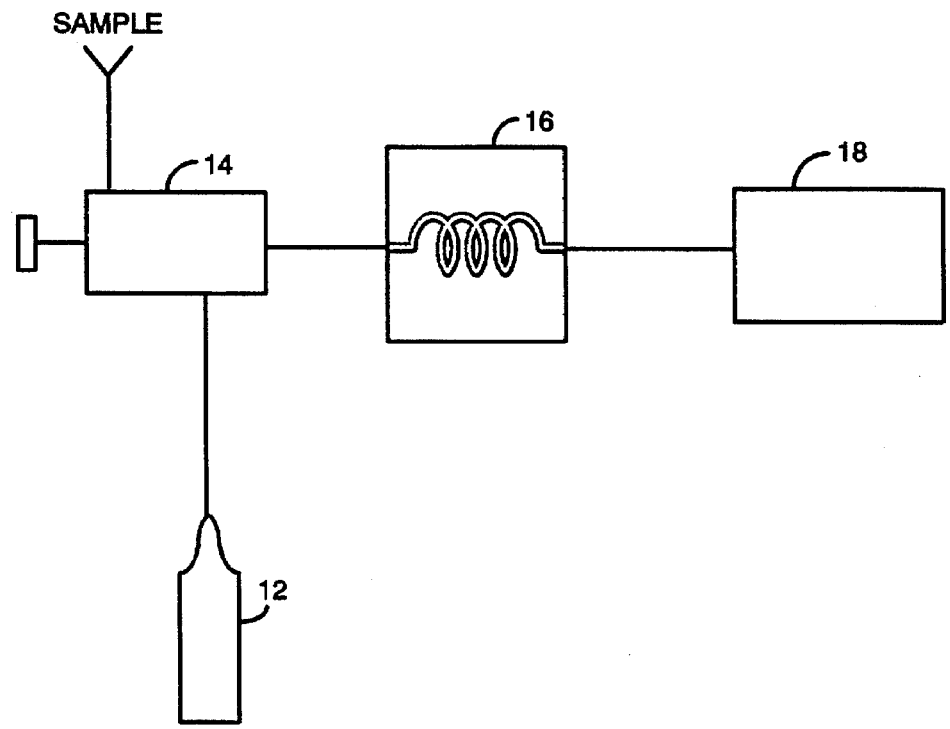
FIG. 1A shows a typical chemical analysis system forming the context of the invention.
Figure 1B:
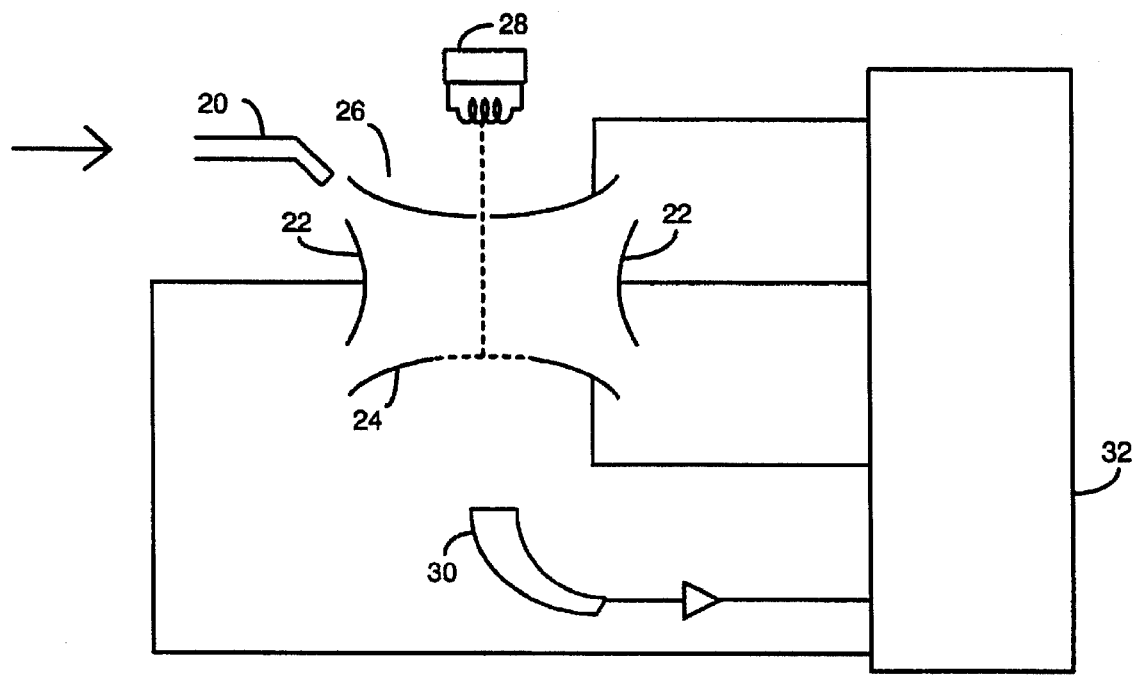
FIG. 1B shows a representative detector.

A suitable context for the practice of the invention may be described with the aid of FIG. 1A and B. The system of FIG. 1A is a gas chromatographic analysis apparatus incorporating a quadrupole mass spectrometer. A representative example of this apparatus includes a carrier gas source 12 which is mixed with a sample at injector 14 and introduced to a GC column 16. The concentration of effluent from the GC column 16 is detected (and further analyzed) in detector apparatus 18. The nature of the detector apparatus varies. For specificity a quadrupole ion trap for mass analysis is shown schematically in FIG. 1B(although various other detectors might utilize the invention). The effluent from GC column 16 is introduced through sample input 20 to the quadrupole ion trap comprising electrodes 22, 24 and 26, electron beam source 28, ion detector 30 and full support electronics package 32. The details of a quadrupole ion trap are well known and need not be further discussed here except for the observation that the operation of this device depends upon fields established by a complex system of electrodes driven at selected frequencies, phases and amplitudes.

In the quadrupole ion trap the electrode shapes employed are approximations to specific quadratic geometries which critically control operation of the trap. As a result of an ionization process, static charge density distributions accumulate on the insulatively coated electrodes and might reach values which will cause arcing resulting in a false signal, or such charge distribution may distort the field, thereby altering the operation of the trap. The thickness of the insulating coating must be sufficiently thin for a given dielectric constant, such that the areal charge density is small enough to have negligible distortion in respect to the electric field distribution. This limit obviously depends upon specific applications, electrode geometry and applied potentials. In the present example an inert fused silica coating with a thickness on the order of less than 0. 1 micron was employed. Coatings of aluminum oxide, silicon nitride or selected semiconductor materials are alternative embodiments.

In the present invention the thickness of the coating must be sufficient to achieve an effective passivation. This lower limit is easily achieved and principally requires that the thickness be of the order of achievable uniformity variations in order to insure that there are no uncoated areas or pinholes.

FIGS. 2A–E, inclusive, and FIGS. 3A–E, inclusive, are respective comparisons of the identical corresponding sample chromatograms in otherwise identical apparatus. For purposes of comparison a comprehensive drug mix test sample was formed from five separate samples of equal masses which, mixed together, were injected into a standard chromographic analyzing apparatus (Saturn model gas chromatograph-mass spectrometer manufactured by Varian Associates, Inc.). Effluent of the column is ionized and is mass analyzed for ions uniquely representative of each of the original sample components and the respective chromatograms are shown for comparison.. In the data acquired from FIGS. 2A–E the standard chromatograph included an ion trap having chromium coated electrodes. The injected sample is analyzed within the ion trap and specific retention time chromatograms for representative ion masses are exhibited in FIGS. 2A–E. In FIGS. 3A–E the same analysis was carried out, the only difference being the fused silica coating of the present invention employed for the electrodes of the ion trap.

The principal difference is dramatically apparent in the absence of tailing in retention time which contributes an asymmetry toward larger retention times. (The difference in position on the abscissa for respective peaks is not significant and (likely) represents a difference in column head pressure for the respective measurements).

The utility of the invention in the context of an ion trap is exemplary and not limiting. Detectors of various types form electric fields in which ions describe certain classes of trajectories. A fraction of the neutral precursors of these ions may be affected by collision with electrodes as well as insulating surfaces. The invention may feature not only coated electrodes which are electrically active, but also insulators which are employed for structural or for electrical purposes. The invention may be used with detectors other than ion traps where the interaction of neutrals with detector surfaces may yield a distortion of data derived from the detector. In the case of an ion trap mass spectrometer the retention time effect from electrode surfaces is observed to distort peak shapes. Insulating members as well as conductors in the interior of the detector may contribute to this particular problem. Other effects may conceivably result in spectral peaks characterizing catalyzed products from collision of sample ions with such surfaces. Detectors of various types in the context of chromatography apparatus can be expected to exhibit similar retention time effects.

Although the invention has been described in conjunction with specific embodiments thereof, it is evident that many alternatives, modifications and variations will be apparent to those skilled in the art in light of the foregoing description, and Applicant is bound only by the appended claims.

What is claimed is:

1. A system for analysis of a sample having constituents, said system comprising a detector having electrodes for defining an interior volume therein and for establishing desired electric fields within said detector interior volume, wherein said electrodes are exposed to said sample constituents and said electrodes comprise an electrical conducting material and an outer surface layer of an inert inorganic non-metallic material deposited on said electrodes.

2. The system of claim 1 wherein said inert inorganic non-metallic material is an insulator.

3. The system of claim 1 wherein said inert inorganic non-metallic material is a semiconductor.

4. The apparatus of claim 2 wherein said insulator is fused silica.

5. The apparatus of claim 2 wherein said insulator is alumina.

6. The apparatus of claim 2 wherein said insulator is silicon nitride.

7. An analytic instrument for chemical analysis of the constituents of a sample, said instrument comprising a detector for responding to ions comprising said constituents, said detector comprising electrodes supporting selected electric fields and said electrodes exposed to said ions, the improvement comprising a coating of an inert inorganic non-metallic material having a thickness which is less than an upper limit thickness selected to support a given areal charge density and which thickness is sufficient to achieve complete passivation of the underlying surface thereof.

8. The analytic instrument of claim 7 wherein said detector further comprises an ion source for creating said ions from said sample.

9. The analytic instrument of claim 7 wherein the areal charge density corresponding to said upper limit thickness has only negligible distorting effect upon said selected electric fields.

* * * * *